United States Patent
Yang

(10) Patent No.: US 11,969,453 B2
(45) Date of Patent: Apr. 30, 2024

(54) HORSERADISH AND CINNAMON MIXED EXTRACT COMPOSITION FOR SUPPRESSION OF AVIAN VIRAL EPIDEMIC DISEASES

(71) Applicant: NAE WOI KOREA., LTD., Seongnam-si (KR)

(72) Inventor: Cheol Ho Yang, Seongnam-si (KR)

(73) Assignee: NAE WOI KOREA., LTD., Seongnam-si (KR)

( * ) Notice: Subject to any disclaimer, the term of this patent is extended or adjusted under 35 U.S.C. 154(b) by 0 days.

(21) Appl. No.: 18/353,992

(22) Filed: Jul. 18, 2023

(65) Prior Publication Data

US 2023/0355700 A1     Nov. 9, 2023

(30) Foreign Application Priority Data

Jun. 14, 2023  (KR) .......................... 10-2023-0076255

(51) Int. Cl.
*A61K 36/00*     (2006.01)
*A61K 36/31*     (2006.01)
*A61K 36/54*     (2006.01)
*A61P 31/14*     (2006.01)

(52) U.S. Cl.
CPC ............... *A61K 36/54* (2013.01); *A61K 36/31* (2013.01); *A61P 31/14* (2018.01); *A61K 2236/15* (2013.01); *A61K 2236/17* (2013.01); *A61K 2236/331* (2013.01); *A61K 2236/333* (2013.01); *A61K 2236/37* (2013.01)

(58) Field of Classification Search
CPC .................................. A61K 36/54; A61K 36/31
See application file for complete search history.

(56) References Cited

U.S. PATENT DOCUMENTS

| | | |
|---|---|---|
| 9,364,511 B2 | 6/2016 | Ovadia |
| 2010/0028268 A1 | 2/2010 | Rosenbloom et al. |
| 2010/0247685 A1 | 9/2010 | Rosenbloom et al. |
| 2022/0105170 A1 | 4/2022 | Finger et al. |

FOREIGN PATENT DOCUMENTS

CN          112385841 A * 2/2021 ............... A23L 2/39

OTHER PUBLICATIONS

Tamam S. M et al., "The Anti-viral and Immunomodulatory Activity of Cinnamon zeylanicum Against "NDV" Newcastle Disease Virus in Chickens", International Journal of Sciences: Basic and Applied Research (IJSBAR) 2017, vol. 32, No. 2, Mar. 29, 2017, pp. 251-262, ISSN 2307-4531.
John S. Oxford et al., "In Vivo Prophylactic Activity of QR-435 Against H3N2 Influenza Virus Infection", American Journal of Therapeutics 2007, vol. 14, Issue. 5, Sep. 2007, pp. 462-468, publication at: https://www.researchgate.net/publication/5953206.

* cited by examiner

*Primary Examiner* — Qiuwen Mi
(74) *Attorney, Agent, or Firm* — Bridgeway IP Law Group, PLLC; Jihun Kim

(57) ABSTRACT

Disclosed is a composition for suppression of avian viral epidemic diseases, including horseradish extract and cinnamon extract. According to the disclosure, a mixed composition of extracts from natural products, and a bactericidal disinfectant composition including the mixed composition are provided to prevent and combat viral diseases damaging bird farms.

4 Claims, 3 Drawing Sheets

HORSERADISH AND CINNAMON MIXED EXTRACT COMPOSITION FOR SUPPRESSION OF AVIAN VIRAL EPIDEMIC DISEASES

CROSS-REFERENCE TO RELATED APPLICATION

This application is based on and claims priority under 35 U.S.C. § 119 to Korean Patent Application No. 10-2023-0076255 filed on Jun. 14, 2023 in the Korean Intellectual Property Office, the disclosure of which is incorporated by reference herein in its entirety.

BACKGROUND

Field

The disclosure relates to a mixed composition of extracts from horseradish and cinnamon to suppress avian viral epidemic diseases, and more particularly to a bactericidal composition for inhibiting viral epidemic diseases, which harm birds, based on a mixed composition of extracts from natural products.

Description of the Related Art

Newcastle disease refers to a viral disease of birds, which is also called avian pneumoencephalitis, and causes respiratory distress and nervousness. Newcastle disease has a high mortality rate in the tropics and subtropics, but may be reversible in adult birds. In particular, young chickens are susceptible to Newcastle disease and almost all die when they get Newcastle disease. Newcastle disease shows various symptoms in turkeys, but rarely shows symptoms in ducks. There is no specific treatment for Newcastle disease, but vaccines are helpful and frequent vaccinations are the best way to prevent this disease. Humans may become infected by touching a bird that has Newcastle disease, but the disease usually progresses to conjunctivitis (inflammation of a mucous membrane on the inside of eyelids) and then goes away. When chickens get this disease, they have a fever, green diarrhea, numbness in their legs, difficulty in breathing, and a mouth and nose full of sticky mucus.

Infectious bursal disease (IBD), also known as Gumboro disease, refers to an acute and contact viral infectious disease for young day-old chicks, which is characterized by contamination of perianal hair with uric acidic diarrhea, and lesions that the bursa of Fabricius becomes swollen and inflamed and then atrophied.

Bronchitis, known as a respiratory disease characterized by inflammation of the capillary bronchi or bronchi the deep sites of lungs, is categorized as acute or chronic according to the duration and severity of symptoms. The infectious bronchitis virus is the first coronavirus to emerge in the world. So far, the known routes of human infiltration are mainly unstructured proteins and accessory proteins which are able to destroy a human immune system.

Porcine epidemic diarrhea (PED), porcine reproductive and respiratory syndrome (PRRS), and chicken infectious bronchitis (IB) are so-called 'productivity diseases,' and in some ways they are of more concern to frontline farmers than African swine fever (ASF) or highly pathogenic avian influenza (AI).

While ASF and highly pathogenic AI may be devastating and result in culling, only a small percentage of farmers actually experience them, the so-called "productivity diseases" are widespread and cause significant economic damage across farms. Therefore, there is a growing call for attention to these diseases that are often overlooked under the shadow of catastrophic diseases.

Actually, animal disease control on the ground is focused on catastrophic diseases. However, what practically hurts the farms is disease that lowers productivity, and there is self-recognition about the lack of control over this disease.

In particular, it is problematic that most of these diseases are classified as three livestock diseases by the domestic animal infectious disease control law. This is because policies of substantially eradicating highly pathogenic AI, ASF and the like diseases have not been promoted, and a report on an outbreak of disease to the quarantine authorities may be followed by quarantine measures such as movement restrictions which cause huge economic damage to farms. Such restrictions make farmers reluctant to report the outbreak of disease. The report on the outbreak of disease may unnecessarily lead to the movement restrictions even when the disease has already been widespread throughout all farms. Similarly, a private disease judgement institution that has received samples from farms and judged three diseases is also burdened.

Therefore, some farms have raised even a radical theory that 'The Ministry of Agriculture, Food and Rural Affairs should honestly admit that there is no national management for diseases except for livestock infectious diseases (tuberculosis, brucellosis, foot-and-mouth disease, Newcastle disease, swine fever, Aujeszky's disease, and avian influenza) for which separate quarantine guidelines have been issued.'

Although these diseases are prevailing and causing substantial damage in production areas as described above, the current situation is not properly grasped letting alone appropriate measures and the damage is getting worse while hushing up problems. In the case of Newcastle disease, there is no specific treatment and thus the measures rely on vaccination. As such, the prevention and measures to these viral diseases are not currently satisfactory, and appropriate prevention and control methods are lacking.

SUMMARY

The disclosure is conceived to solve the foregoing problems, and an aspect of the disclosure is to provide a mixed composition of extracts from natural products so as to prevent and combat viral diseases damaging bird farms.

Another aspect of the disclosure is to provide a mixed composition of extracts from natural products so as to prevent and combat three viral diseases damaging bird farms.

According to an embodiment of the disclosure, there is provided a composition for suppression of avian viral epidemic diseases, which contains horseradish extract and cinnamon extract.

Further, it is characterized in that a causative virus of the avian viral epidemic diseases is a Newcastle disease virus.

Further, it is characterized in that causative virus of the avian viral epidemic diseases is an avian infectious bronchitis virus.

Further, it is characterized in that a causative virus of the avian viral epidemic diseases is infectious bursal disease virus.

Further, it is characterized in that the horseradish extract and the cinnamon extract are extracted from horseradish, cinnamon or a mixture thereof by hot water extraction or ethanol extraction.

Further, it is characterized in that the horseradish extract is a solution prepared by drying and pulverizing horseradish into horseradish powder, adding 10 to 20 parts by weight of the horseradish powder to 100 parts by weight of water, and heating the water in a temperature range of 70 to 90° C. until the amount of water is reduced by half.

Further, it is characterized in that the cinnamon extract is a solution prepared by adding 10 to 20 parts by weight of a dried cinnamon wood to 100 parts by weight of water, heating the water in a temperature range of 70 to 90° C. until the amount of water is reduced by half, and removing the cinnamon wood.

BRIEF DESCRIPTION OF THE DRAWINGS

The above and/or other aspects will become apparent and more readily appreciated from the following description of embodiments, taken in conjunction with the accompanying drawings, in which.

DETAILED DESCRIPTION OF EMBODIMENTS

Figure 1:
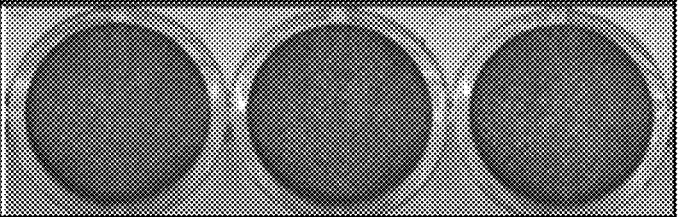
FIG. 1 shows result images of experiments based on compositions according to an embodiment of the disclosure to check a bactericidal effect on Newcastle disease viruses.

The disclosure relates to compositions that contain horseradish extract and cinnamon extract to inhibit avian viral epidemic diseases.

Below, the disclosure will be described in detail with reference to the accompanying drawings.

According to the disclosure, the compositions that contain horseradish extract and cinnamon extract to inhibit avian viral epidemic diseases are highly effective in suppressing three infectious diseases causing great damage to bird farms.

An aspect of the disclosure relates to compositions for inhibiting avian viral epidemic diseases, which are effective in suppressing Newcastle disease virus as one of causative viruses of the avian viral epidemic diseases.

Further, an aspect of the disclosure relates to compositions for inhibiting avian viral epidemic diseases, which are effective in suppressing avian infectious bronchitis virus as one of causative viruses of the avian viral epidemic diseases.

Further, an aspect of the disclosure relates to compositions for inhibiting avian viral epidemic diseases, which are effective in suppressing infectious bursal disease virus as one of causative viruses of the avian viral epidemic diseases.

Contagious diseases caused by these three viruses are not as widely known as African Swine Fever (ASF) or highly pathogenic AI, but they are known to cause greater damage to farms and there are no specific prevention and treatment other than vaccines.

The disclosure relates to a mixed composition of extracts from the natural products such as horseradish and cinnamon, as a substance having an outstanding bactericidal effect on three viruses that cause the above troublesome avian viral diseases.

According to an embodiment of the disclosure, the horseradish extract and the cinnamon extract may be extracted from horseradish, cinnamon or a mixture thereof by hot water extraction or ethanol extraction, but not limited thereto. Alternatively, the horseradish extract and the cinnamon extract may be extracted by any extraction method generally used in the art to which the disclosure pertains.

According to an embodiment of the disclosure, it is characterized in that the horseradish extract is a solution prepared by drying and pulverizing horseradish into horseradish powder, adding 10 to 20 parts by weight of the horseradish powder to 100 parts by weight of water, and heating the water in a temperature range of 70 to 90° C. until the volume is reduced by half.

Further, according to an embodiment of the disclosure, it is characterized in that the cinnamon extract includes a solution prepared by adding 10 to 20 parts by weight of a dried cinnamon wood to 100 parts by weight of water, heating the water in a temperature range of 70 to 90° C. until the volume is reduced by half, and removing the cinnamon wood.

An aspect of the disclosure is to provide a composition in which the cinnamon extract and the horseradish extract are mixed. It was confirmed that the mixed extract prepared by mixing the cinnamon extract and the horseradish extract has an outstanding bactericidal effect on viruses causing avian viral epidemic diseases.

According to an embodiment of the disclosure, the horseradish and the cinnamon extract may be stored as liquid in a microcapsule.

According to an embodiment of the disclosure, the microcapsule may be varied in diameter to differentiate the speed at which an antibacterial substance is released from the microcapsule, thereby continuously implementing an antibacterial function for a long time against avian infectious viruses.

In more detail, a first group of the microcapsules having a small outer diameter, a second group of the microcapsules having a medium outer diameter, and a third group of the microcapsules having a large outer diameter are arranged by predetermined proportions, so that duration of releasing liquid from the microcapsules can be differently controlled based on the difference in diameter among the microcapsules, thereby implementing the antibacterial function against virus for at least one year and up to five years Further, the first group has an outer diameter of 3±3 μm, the second group has an outer diameter of 9±3 μm, the third group has an outer diameter of 15±3 μm, and the proportions of the first group, the second group, and the third group to be mixed are the same on being calculated based on volume.

Further, the film thickness of the microcapsule having an outer diameter of 15 to 18 μm is controlled so that the antibacterial substance can be released from the microcapsule within 6 months, and the film thickness of the microcapsule having an outer diameter of 12 to 15 μm is controlled so that the antibacterial substance can be released from the microcapsule within 1 year, the film thickness of the microcapsule having an outer diameter of 9 to 12 μm is controlled so that the antibacterial substance can be released from the microcapsule within 1 to 2 years, the film thickness of the microcapsule having an outer diameter of 6 to 9 μm is controlled so that the antibacterial substance can be released from the microcapsule within 2 to 3 three years, the film thickness of the microcapsule having an outer diameter of 3 to 6 μm is controlled so that the antibacterial substance can be released from the microcapsule within 3 to 4 years, and the film thickness of the microcapsule having an outer diameter of 0.5 to 3 μm is controlled so that the antibacterial substance can be released from the microcapsule within 4 to 5 years.

The microcapsules that contain the mixed liquid compositions of horseradish extract and cinnamon extract may be manufactured by a general method typically used in the art to which this technology pertains, and there are no particular limitations to the manufacturing method.

According to an embodiment of the disclosure, the microcapsule filed with the mixed composition of extract according to the disclosure may include a core to store and provide a core material, i.e., the mixed extract located inside the microcapsule; and an outer skin as a film for surrounding the core.

The material of the outer skin may include one of melamine resin, urethane resin, fumed silica, gelatin, polyphosphates, mixtures of polysaccharides, alginates, chitosan, pectin, starch, cellulose, methylcellulose, ethylcellulose, hydroxyethyl cellulose, carboxymethyl cellulose, vegetable protein, animal protein, agar, albumin, xanthan, gellan gum, or a mixture of two or more of them.

Below, embodiments of the disclosure will be described in more detail. However, these embodiments are intended only to illustrate the disclosure and are not to be construed as limiting the scope of the disclosure, and it will be understood by a person having ordinary knowledge in the art that substitutions and modifications can be made in a part of the embodiments without departing from the technical spirit of the disclosure.

Embodiment 15 parts by weight of dried cinnamon wood were added to of 100 parts by weight of water, and heated at a temperature of 80° C. until the amount of water was reduced by half, thereby preparing cinnamon extract liquid.

Horseradish was dried and pulverized into horseradish powder, and 15 parts by weight of the horseradish powder were added to 100 parts by weight of water and heated at a temperature of 80° C. until the amount of water was reduced by half, thereby preparing horseradish extract liquid.

The cinnamon extract liquid and the horseradish extract liquid were mixed in a weight ratio of 1:1 to prepare mixed extract liquid.

The mixed extract liquid used as a core material and melamine used as an outer skin material are mixed and then stirred at room temperature for 1 hour, thereby manufacturing the microcapsule that contains the mixed extract liquid.

Experimental Examples

Antiviral tests were conducted against the three viruses of avian viral epidemic diseases by using the mixed extract microcapsules manufactured as above.

1. Newcastle Disease Virus
Virus type: Newcastle disease virus
Test Method: ASTM E1052
Test concentration: 25% with contact for 2 hours
The test results are shown in Table 1 and Table 2 below.

TABLE 1

| Test results | | |
|---|---|---|
| Test concentration (condition) | Log reduction | Virus reduction rate (%) |
| 25% (contact for 2 hours) | 1.7 | 97.8 |

TABLE 2

| Virus quantified value (PFU/ml) | |
|---|---|
| Virus concentration of comparative example | $4.0 \times 10^7$ |
| Virus concentration of embodiment | $8.6 \times 10^5$ |

Compared to the number of plaques on virus-infected host cells in the comparative example (non-contact sample with mixed extract microcapsule agent), the log reduction in the number of plaques on virus-infected host cells in the embodiment (contact sample with mixed extract microcapsule agent) was 1.7 and the virus reduction rate was 97.8%.

Results in Reduction (%)
90% or more (less than 99%) for log reduction of 1 or higher
99% or more (less than 99.9%) for log reduction of 2 or higher
99.9% or more (less than 99.99%) for log reduction of 3 or higher
99.99% or more (less than 99.999%) for log reduction of 4 or higher
99.999% or more for log reduction of 5 or higher As shown in the results in Table 1 and Table 2, the viral concentration of the embodiment is 2% of the viral concentration of the comparative example, thereby having a good antibacterial efficacy.

FIG. 1 shows result images of an antibacterial test based on compositions according to an embodiment of the disclosure against Newcastle disease viruses. In both the inoculation tests of $10^{-4}$ and $10^{-5}$, the embodiments show significantly lower concentrations of bacterial expression compared to the comparative examples.

2. Avian Infectious Bronchitis Virus
Virus Type: Infectious bronchitis virus
Test Method: ASTM E1052
Test concentration: 25% with contact for 2 hours
The test results are shown in Table 3 and Table 4.

TABLE 3

| Test results | | |
|---|---|---|
| Test concentration (condition) | Log reduction | Virus reduction rate (%) |
| 25% (contact for 2 hours) | 1.2 | 93.3 |

TABLE 4

| Virus quantified value (PFU/ml) | |
|---|---|
| Virus concentration of comparative example | $4.1 \times 10^7$ |
| Virus concentration of embodiment | $2.8 \times 10^6$ |

Compared to the number of plaques on virus-infected host cells in the comparative example (non-contact sample with mixed extract microcapsule agent), the log reduction in the number of plaques on virus-infected host cells in the embodiment (contact sample with mixed extract microcapsule agent) was 1.2 and the virus reduction rate was 93.3%.

As shown in the results in Table 3 and Table 4, the viral concentration of the embodiment is 6.8% of the viral concentration of the comparative example, thereby having a good antibacterial efficacy.

Figure 2:
FIG. 2 shows result images of experiments based on compositions according to an embodiment of the disclosure to check a bactericidal effect on avian infectious bronchitis viruses.

FIG. 2 shows result images of an antibacterial test based on compositions according to an embodiment of the disclosure against the infectious bronchitis virus. In both the inoculation tests of $10^{-4}$ and $10^{-5}$, the embodiments show significantly lower concentrations of bacterial expression compared to the comparative examples.

3. Infectious Bursal Disease Virus
Virus Type: Infectious bursal disease virus
Test Method: ASTM E1052
Test Concentration: 25% with contact for 2 hours
The test results are shown in Table 5 and Table 6.

TABLE 5

Test results

| Test concentration (condition) | Log reduction | Virus reduction rate (%) |
| --- | --- | --- |
| 25% (contact for 2 hours) | 1.4 | 95.6 |

TABLE 6

| Virus quantified value (PFU/ml) | |
| --- | --- |
| Virus concentration of comparative example | $8.9 \times 10^7$ |
| Virus concentration of embodiment | $3.9 \times 10^6$ |

Compared to the number of plaques on virus-infected host cells in the comparative example (non-contact sample with mixed extract microcapsule agent), the log reduction in the number of plaques on virus-infected host cells in the embodiment (contact sample with mixed extract microcapsule agent) was 1.4 and the virus reduction rate was 95.6%.

As shown in the results in Table 5 and Table 6, the viral concentration of the embodiment is 4.3% of the viral concentration of the comparative example, thereby having a good antibacterial efficacy.

Figure 3:
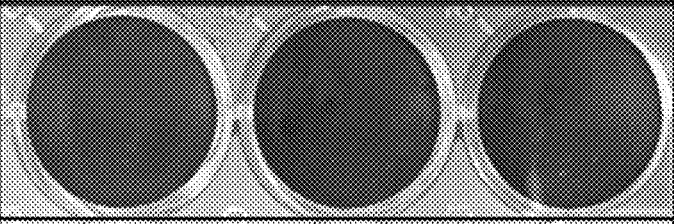
FIG. 3 shows result images of experiments based on compositions according to an embodiment of the disclosure to check a bactericidal effect on infectious bursal disease viruses.

FIG. 3 shows result images of an antibacterial test based on compositions according to an embodiment of the disclosure against the infectious bursal disease virus. In both the inoculation tests of $10^{-4}$ and $10^{-5}$, the embodiments show significantly lower concentrations of bacterial expression compared to the comparative examples. In particular, in the inoculation test of $10^{-5}$, the embodiment shows bacterial expression almost identical to that of uninfected bacteria.

According to the disclosure, there are provided a mixed composition of extracts from natural products, and a bactericidal disinfectant composition including the mixed composition, so as to prevent and combat viral diseases damaging bird farms.

Although specific embodiments of the disclosure have been described in detail, the embodiments are intended to illustrate the disclosure, and it will be apparent that the disclosure is not limited to those embodiments and modifications and improvements can be made by a person having ordinary knowledge in the art without departing from the spirit of the disclosure.

What is claimed is:

1. A composition for suppression of avian viral epidemic diseases, comprising horseradish extract and cinnamon extract,
wherein the horseradish extract comprises a solution prepared by drying and pulverizing horseradish into horseradish powder, adding 10 to 20 parts by weight of the horseradish powder to 100 parts by weight of water, and heating the water in a temperature range of 70 to 90° C. until an amount of the water is reduced by half, and
wherein the cinnamon extract comprises a solution prepared by adding 10 to 20 parts by weight of cinnamon wood to 100 parts by weight of water, heating the water in a temperature range of 70 to 90° C. until an amount of the water is reduced by half, and removing the cinnamon wood.

2. The composition of claim 1, wherein a causative virus of the avian viral epidemic diseases comprises a Newcastle disease virus.

3. The composition of claim 1, wherein a causative virus of the avian viral epidemic diseases comprises an avian infectious bronchitis virus.

4. The composition of claim 1, wherein a causative virus of the avian viral epidemic diseases comprises infectious bursal disease virus.

* * * * *